US012611679B2

(12) United States Patent
Mitschulat et al.

(10) Patent No.: US 12,611,679 B2
(45) Date of Patent: Apr. 28, 2026

(54) SYSTEM FOR BLOOD CELL SEPARATION

(71) Applicant: Fresenius Kabi Deutschland GmbH, Bad Homburg (DE)

(72) Inventors: Heike Mitschulat, Diemelstadt (DE); Anke Hannig, Hilden (DE); Michael Schwalm, Alsfeld (DE); Patrick Schwalm, Alsfeld (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 980 days.

(21) Appl. No.: 17/542,684

(22) Filed: Dec. 6, 2021

(65) Prior Publication Data

US 2022/0184638 A1     Jun. 16, 2022

(30) Foreign Application Priority Data

Dec. 10, 2020    (EP) .................................... 20213093

(51) Int. Cl.
*B04B 5/04* (2006.01)
*A61M 1/02* (2006.01)
*B04B 11/02* (2006.01)

(52) U.S. Cl.
CPC ............ *B04B 5/0442* (2013.01); *B04B 11/02* (2013.01); *A61M 1/0259* (2013.01)

(58) Field of Classification Search
CPC ......... B04B 5/0442; B04B 11/02; B04B 5/12; B04B 2005/045; A61M 1/0259;
(Continued)

(56) References Cited

U.S. PATENT DOCUMENTS 2,664,085 A * 12/1953 Ryan .................... A61M 5/1411
604/252
3,664,339 A     5/1972 Santomieri
(Continued)

FOREIGN PATENT DOCUMENTS

CN          1237113 A      12/1999
CN          1322146 A      11/2001
(Continued)

OTHER PUBLICATIONS

Communication pursuant to Article 94(3) EPC in connection with EP appl. 20213093.6 dated Apr. 26, 2024.

*Primary Examiner* — Claire X Wang
*Assistant Examiner* — Shuyi S. Liu
(74) *Attorney, Agent, or Firm* — Cook Alex Ltd

(57)            ABSTRACT

A system for blood cell separation, comprising:
  a separation chamber (10) comprising an inlet port for blood (12), an outlet port for plasma (14) and at least an outlet port for cellular blood components (16) for the separation of whole blood;
  a blood pump (20) for pumping whole blood into the inlet port for blood (12);
  a plasma pump (22) for pumping plasma and/or target cells from the outlet port for plasma (14) out of the separation chamber (10);
  a red blood cell tube (30) comprising a first end (32) and a second end (34), wherein the first end (32) of the red blood cell tube (30) is connected to the outlet port for cellular blood components (16) for allowing red blood cells to leave the separation chamber (10); and
  a drip chamber (40) comprising a reservoir (42) and an inlet (46), wherein the second end (34) of the red blood cell tube (30) is connected to the inlet (46), wherein the second end (34) of the red blood cell tube (30) extends
(Continued)

into the volume of the reservoir (42) for pressure equalization during pumping from the outlet port for plasma (14).

5 Claims, 4 Drawing Sheets

(58) Field of Classification Search
CPC .. A61M 2202/0407; A61M 2202/0437; A61M 2202/0439; A61M 1/382; A61M 5/1411; A61M 1/029; A61M 1/3696; A61M 1/38; A61M 2202/0413; A61M 1/3693; A61M 1/36225; A61M 1/362266; A61M 1/3639; A61M 1/3496; A61M 1/303; A61M 1/304
See application file for complete search history.

(56)                   References Cited

U.S. PATENT DOCUMENTS

| | | | |
|---|---|---|---|
| 5,734,464 A * | 3/1998 | Gibbs ................ | G01N 21/3151 |
| | | | 356/39 |
| 2019/0143023 A1* | 5/2019 | Yuds ................... | A61M 1/3627 |
| | | | 604/4.01 |
| 2019/0167889 A1* | 6/2019 | Mitschulat .......... | A61M 1/3696 |
| 2019/0290837 A1 | 9/2019 | Warta | |

FOREIGN PATENT DOCUMENTS

| | | |
|---|---|---|
| EP | 3509663 A1 | 7/2019 |
| FR | 1207966 A | 2/1960 |
| GB | 758096 A | 9/1956 |

* cited by examiner

SYSTEM FOR BLOOD CELL SEPARATION

CROSS-REFERENCE TO RELATED APPLICATION

This application claims priority to and the benefit of European Application No. 20213093.6 filed on Dec. 10, 2020, the disclosure of which is incorporated herein by reference in its entirety.

The invention relates to a system for blood cell separation according to the preamble of claim 1 and to a drip chamber for use in such a system.

A system of this kind comprises a separation chamber comprising an inlet port for blood, and outlet ports for plasma and cellular blood components for the separation of whole blood. The system also comprises a blood pump for pumping whole blood into the inlet port for blood, and a plasma pump, or a cell pump for pumping plasma and/or target cells out of the separation chamber. The system furthermore comprises a red blood cell tube comprising a first end and a second end, wherein the first end of the red blood cell tube is connected to the outlet port for cellular blood components for allowing red blood cells to leave the separation chamber. Also, the system comprises a drip chamber comprising a reservoir and an inlet, wherein the second end of the red blood cell tube is connected to the inlet.

A system of this kind may generally be used in the field of blood apheresis, where blood is withdrawn from a donor/patient. The blood, which can be also referred to as whole blood, is separated by such a system into its major components, i.e. separated into plasma and erythrocytes, and the remainder is reinfused into the donor/patient. Depending on the application, abnormal, pathogenic components can be removed with the plasma in a therapeutic plasma exchange procedure; or abnormal erythrocytes can be removed and exchanged by healthy cells in a red blood cell exchange procedure.

The separation chamber is usually comprised in a centrifuge unit that is configured to separate the blood components by density and size. The end product of the blood centrifugation are sedimented erythrocytes at the outside of the separation chamber, the buffycoat containing MNCs (MNC mononucleated cells), i.e. lymphocytes and monocytes, stem cells, and platelets in the middle and the blood plasma at the inside of the separation chamber.

An example for a known blood cell separation system is the COM.TEC® cell separator, which is described in EP 3 509 663 A1.

In the separation phase, the whole blood is separated in the separation chamber into a red blood cell layer, a platelet-rich plasma, PRP, and a mononuclear cell, MNC, layer, where the MNC layer is accumulated in the separation chamber, while the red blood cell layer and the PRP are returned to the patient/donor.

The separation phase is followed by a so-called spillover phase, where the MNC layer is pumped out of the separation chamber either volume controlled or—more precisely—up to sensing means, such as an optical sensor that can control a collection clamp. When cells are detected the spillover phase is stopped and the so-called buffycoat phase is started, where the path back to the patient is closed and the path up to a collection container is opened for collecting the MNC.

However, during the spillover phase, where the MNC layer is pumped out of the separation chamber, a negative pressure within the separation chamber pulls back fluid to equalize the negative pressure, which causes (i) at first the red blood cell layer to be pulled into the separation chamber, and (ii) secondly the whole blood to be pulled into the separation chamber.

Unfortunately, the negative pressure pulling back solutions into the separation chamber makes the accurate collection of, in particular, smaller volumes of a more compact fraction of target cells difficult.

Therefore, it is an object of the instant invention to provide a system for blood cell separation which allows for an easy and accurate collection of target cells, and which is also able to accurately collect smaller volumes of higher concentrated target cells.

This object is achieved by means of a system comprising the features of claim 1.

Accordingly, the second end of the red blood cell tube extends into the volume of the reservoir for pressure equalization during pumping from the outlet port for plasma, such as for example during pumping the MNC layer.

The herein described system for blood cell separation can be used in the above referenced automated COM.TEC® cell separator.

Hence, in examples the system can further comprise a front panel with a user interface, several pumps, automatic clamps and detector devices comprising optical sensors for monitoring fluid streams, an iv pole for attaching saline and anticoagulant bags, prime bag, and collection containers for target cells and plasma, etc. The separation chamber can be comprised in a centrifuge compartment, which comprises a rotor with a mechanism to install a chamber holder for holding the separation chamber. The separation chamber and the containers can be connected to each other by a tubing system comprising several tubes. The pumps utilized in the system can be peristaltic pumps and transport the blood, blood fractions, and solutions between the aforementioned parts of the system. The system can be controlled by a processor device.

As suggested by the invention, the second end of the red blood cell tube extends into the volume of the reservoir for pressure equalization during pumping from the outlet port for plasma.

Herein, the term "drip chamber" can be used to refer to a device that allows to retain gas such as air so that it is not passed downstream. In the present system the drip chamber ensures that the red blood cells and/or the plasma returned to the donor/patient are free of air.

The term "reservoir" can be used to refer to a structure such as a container of regular or irregular shape to hold fluid. In contrast to the prior art, where the red blood cell tube is arranged with its second end above the volume of the reservoir, the second end of the red blood cell tube extends into the volume of the reservoir. Hence, depending on the fluid level inside the reservoir, the second end of the red cell tube can be fully submerged in the fluid inside the reservoir, i.e. being located below the fluid level.

Advantageously, this arrangement of the second end of the red blood cell tube extending into the volume of the reservoir allows to increase the reservoir volume for the red cell fraction, which in turn leads to avoiding the use of whole blood for pressure equalization. As a result, the target cell layer will be spilled over as a more compact layer and thereby to allow the collection of the same target cells within a smaller volume compared to the spillover with a prior art system, where the second end of the red blood cell tube is not extending into the volume of the reservoir of the drip chamber. Also, by increasing the reservoir volume for the red cell fraction by means of the second end of the red blood cell tube extending into the volume of the reservoir for pressure equalization during pumping the MNC layer, existing systems can be easily improved, since the current functional design of neither the separation chamber nor the drip chamber needs to be modified.

In an example, the second end of the red blood cell tube extends at least into 20% of the volume of the reservoir.

Here, the opening at the second end of the red blood cell tube extends at least into 20% of the volume of the reservoir. Consequently, when the reservoir is filled above 80% with fluid the opening at the second end of the red blood cell tube will be submerged in the fluid, which means that the opening will be located below the fluid level.

In further examples, the second end of the red blood cell tube extends at least into 50% and 80% of the volume of the reservoir.

In an example, the second end of the red blood cell tube extends to a bottom surface of the reservoir.

The bottom surface might be located in gravity direction opposite the inlet of the reservoir. Hence, in this example, the opening at the second end of the red cell tube might essentially extend as far as possible into the reservoir, so that the opening at the second end is still submerged into the fluid inside the reservoir, even at a low fluid level.

In an example, the second end of the red blood cell tube extends to an outlet opening in the bottom surface of the reservoir.

The term "outlet opening" can be used to refer to an opening in the bottom surface of the reservoir through which the fluid inside the reservoir can be returned to the patient/donor.

In an example, the system comprises a lid configured to be placed on the reservoir for covering the reservoir, wherein the inlet is arranged in the lid, and wherein the second end of the red blood cell tube extends through the lid.

The lid can cover the reservoir to prevent dirt or other contaminations from entering the reservoir. The inlet can be an essentially round opening having a diameter slightly larger than the outer diameter of the red cell tube so that the red cell tube can extend through the opening into the reservoir and can be held in position.

In an example, the drip chamber comprises a second inlet configured to be connected to a plasma tube which carries fluid from the outlet port for plasma into the reservoir.

In addition to fluid from the red blood cell tube entering though the inlet, fluid from the plasma tube can also enter the reservoir through the second inlet.

Depending on the operational mode of the system, fluid from the plasma tube can be re-introduced into the patient/donor during the spillover phase.

In an example, the separation chamber comprises a further outlet port for cellular blood components.

Advantageously, different versions of separation chambers can be used with the system described herein.

The object is also achieved by a drip chamber for a system for blood cell separation, in particular for a system as described herein, comprising: a reservoir and an inlet, wherein the inlet is connectable to a second end of a red blood cell tube, and wherein the second end of the red blood cell tube extends into a volume of the reservoir for pressure equalization during pumping by the system.

The advantages and advantageous embodiments described above for the system equally apply also to the drip chamber, such that it shall be referred to the above.

The idea underlying the invention shall subsequently be described in more detail with reference to the embodiments shown in the figures. Herein:

Figure 1:
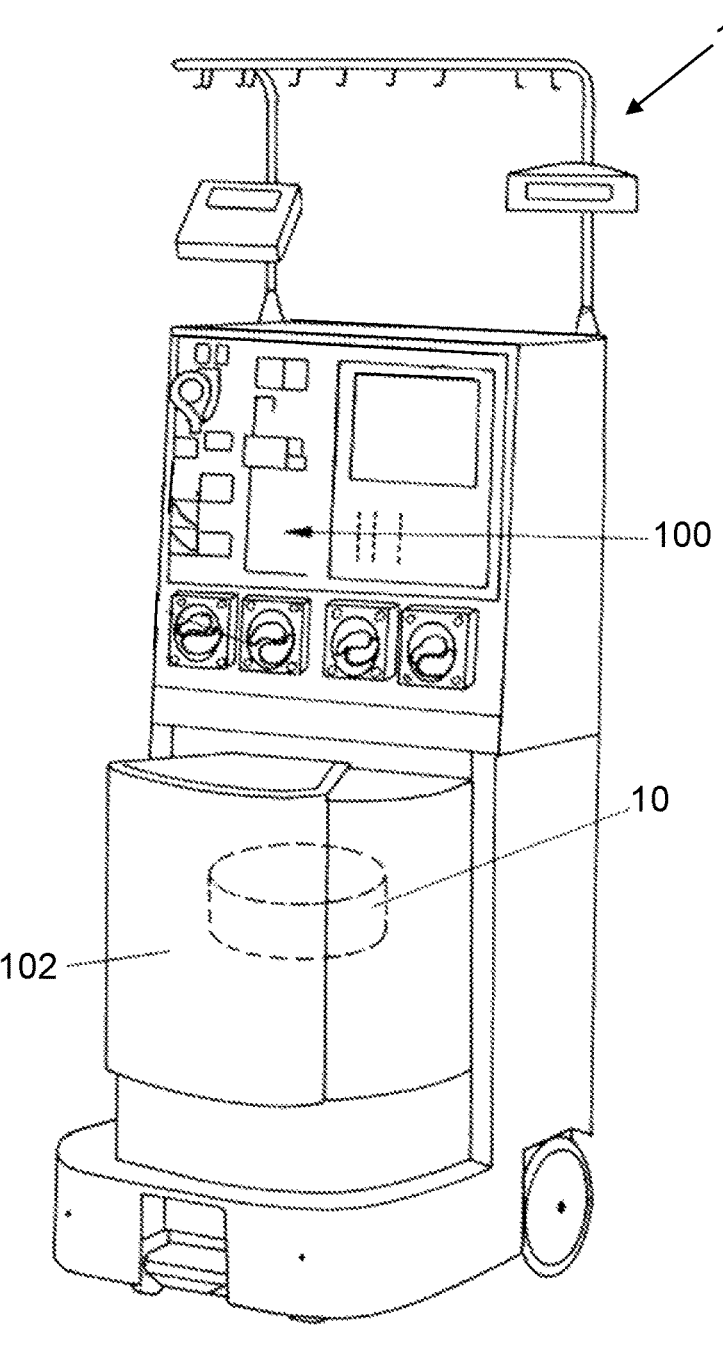
FIG. 1 shows a schematic view of a system for blood cell separation which is commonly used in the prior art.

FIG. 1 shows a schematic view of an exemplary system 1 for blood cell separation. The system 1 is mobile by means of wheels that are attached to a housing. The shown system 1 comprises a front panel 100 with automatic clamps, pumps and a user interface. The shown system 1 also comprises a centrifuge compartment 102 where the separation chamber 10 is located.

Figure 2A:
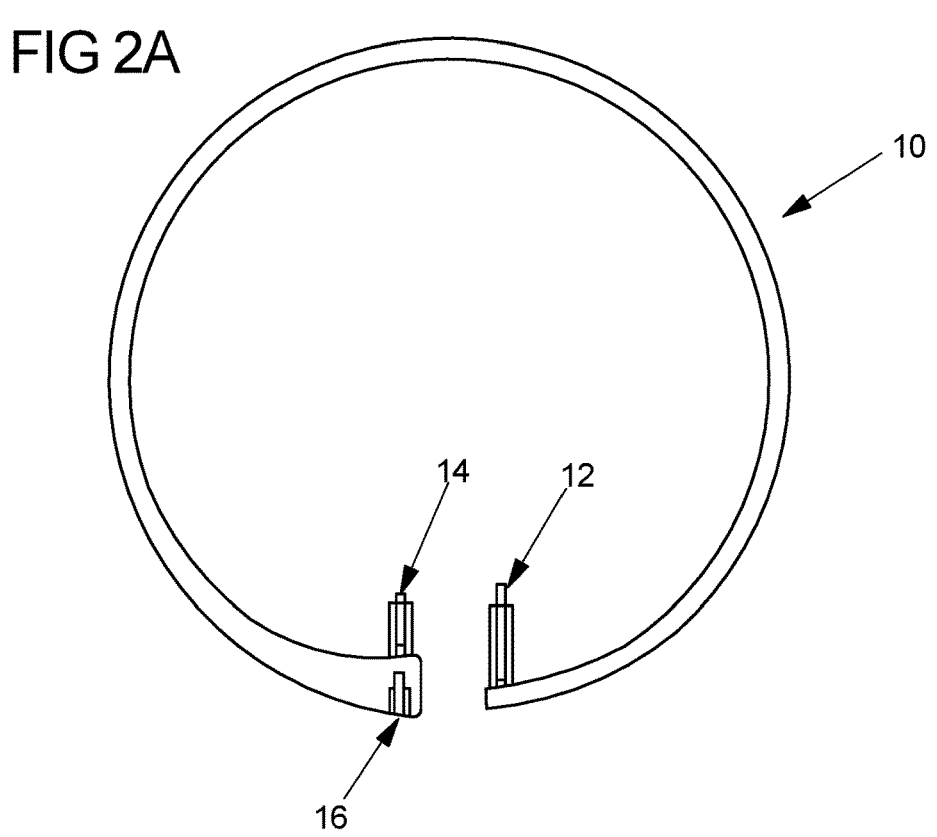
FIGS. 2A, 2B show schematic views of separation chambers which are commonly used in the prior art.

FIG. 2A shows a schematic view of an exemplary separation chamber 10. The separation chamber 10 shown in FIG. 2A can be the separation chamber 10 previously shown in FIG. 1. The separation chamber 10 can be essentially cylindrical and can be used in conjunction with a centrifugal unit (not shown in FIG. 2A) to spin blood in the separation chamber 10 to separate blood in the separation chamber 10 into its components. The separation chamber 10 comprises an inlet port for blood 12 through which whole blood from a donor/patient can be pumped into the separation chamber 10. FIG. 2A also shows that in orbital direction opposite the inlet port for blood 12 on a flared section of the separation chamber 10, an outlet port for plasma 14 and an outlet port for cellular blood components 16 are located. During the separation process, the whole blood is separated into plasma available at the outlet port for plasma 14 and red blood cells available at the outlet port for cellular blood components 16. Between plasma and the red blood cells, a so-called buffy-coat is located comprising the mononuclear cell, MNC, layer with the target cells.

Figure 2B:
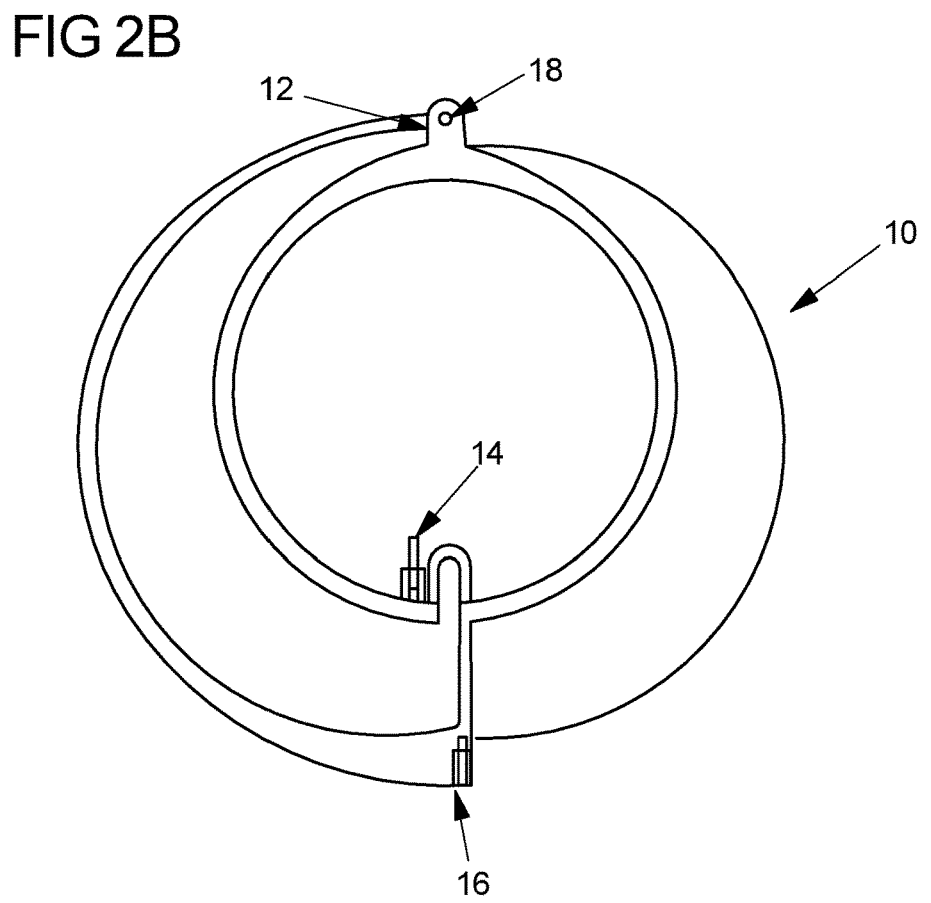

FIG. 2B shows a schematic view of another exemplary separation chamber 10. In addition to an inlet port for blood 12, an outlet port for plasma 14, and an outlet port for cellular blood components 16, the shown separation chamber 10 comprises a further outlet port for cellular blood components 18.

Figure 3A:
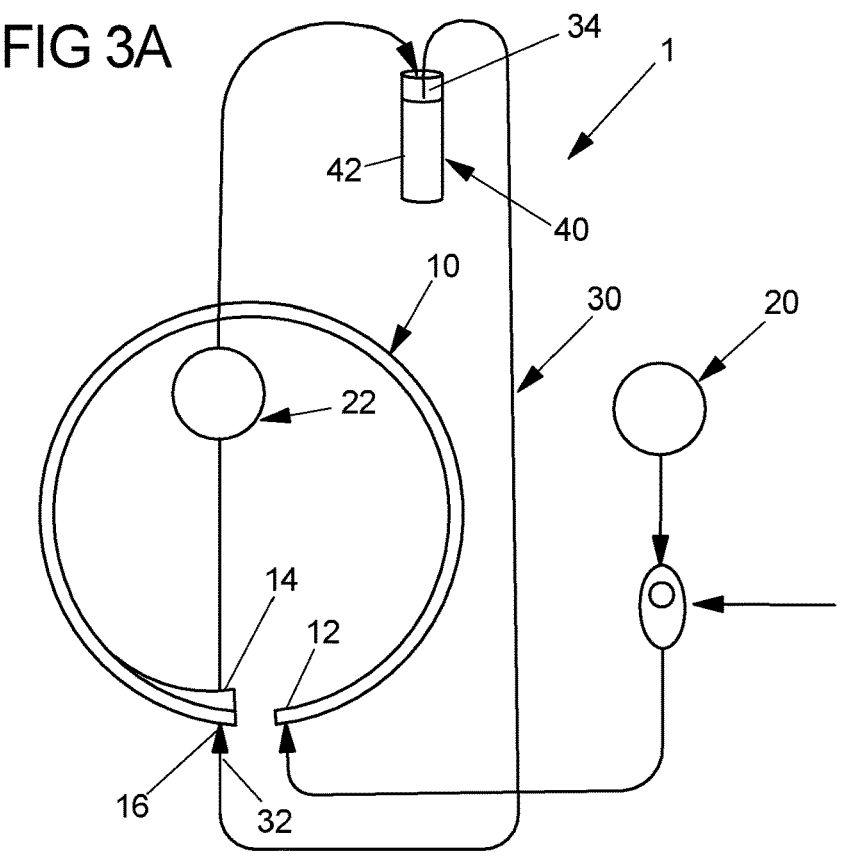
FIGS. 3A, 3B show schematic views of systems for blood cell separation according to embodiments of the invention.

FIG. 3A shows the system for blood cell separation 1 according to an embodiment. As shown, the system 1 comprises a separation chamber 10, which could be the separation chamber 10 as shown in FIG. 2A. The separation chamber 10 comprises an inlet port for blood 12, an outlet port for plasma 14 and an outlet port for cellular blood components 16 for the separation of target cells from whole blood. The system also comprises a blood pump 20 for pumping whole blood into the inlet port for blood 12 and a plasma pump 22 for pumping a fluid, i.e. plasma and the mononuclear cell, MNC, layer comprising the target cells from the outlet port for plasma 14 out of the separation chamber 10.

In FIG. 3A a red blood cell tube 30 is connected to the port for cellular blood components 16 for allowing red blood cells to leave the separation chamber 10. As shown in FIG. 3A, the red blood cell tube 30 comprises a first end 32 and a second end 34, wherein the first end 32 of the red blood cell tube 30 is connected to the port for cellular blood components 16, whereas the second end 34 is in contact with a drip chamber 40 of the system 1. As schematically shown, the second end 34 of the red blood cell tube 30 extends into the volume of the reservoir 42 for pressure equalization during pumping the MNC layer, which will be described in greater detail with reference to FIGS. 5A and 5B.

As described above, with reference to FIGS. 2A and 2B, whole blood is separated into its components during the separation phase. Essentially, the red blood cell and plasma fractions are separated in the separation chamber 10. During this so-called separation step an outer layer, which comprises the red blood cells, and an inner layer, which comprises the blood plasma, are formed. The buffycoat comprising the mononuclear cell, MNC, layer with the target cells is accumulated as a further layer between the red blood cell and plasma fractions in the separation chamber 10.

Once the separation phase is finished, the spillover phase starts where the plasma is pumped by a plasma pump 22 into the reservoir 42 of the drip chamber 40 as indicated by the arrow in FIG. 3A. Once target cells are detected in the plasma, for example by means of an optical sensor (not shown) that is located in the tubing section in proximity to the plasma pump 22, a collection clamp (not shown) could divert the stream of fluid going from the outlet port for plasma 14 to the drip chamber 40 as shown in FIG. 3A to a stream of fluid going from the outlet port for plasma 14 to a collection container (not shown) where the target cells are collected.

The flow rates of blood going into the separation chamber 10 and the plasma going out of the separation chamber 10 cause a negative pressure within the separation chamber 10 during the spillover phase.

The arrangement of the second end 34 of the red blood cell tube 30 extending into the volume of the reservoir 42 of the drip chamber 40 allows to increase the reservoir volume for the red cell fraction, which in turn leads to avoiding the use of whole blood for pressure equalization. As a result, the target cell layer can be spilled over as a more compact layer to allow the collection of a smaller volume with a more compact cell fraction compared to the spillover with a prior art system, where the second end of the red blood cell tube is not extending into the volume of the reservoir of the drip chamber.

Figure 3B:
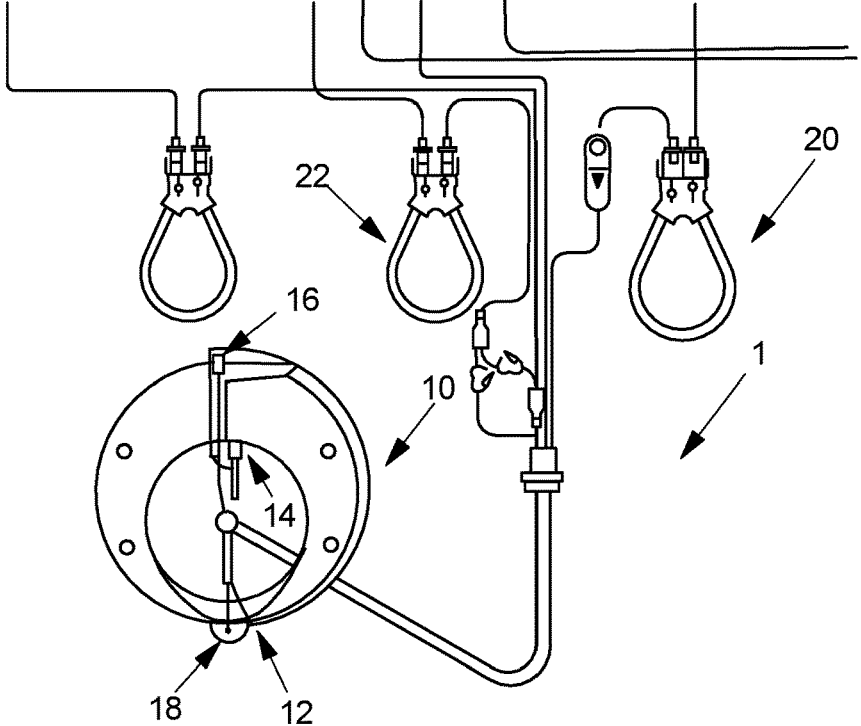

FIG. 3B shows another embodiment of at least part of the system for blood cell separation 1. In the embodiment shown in FIG. 3B, the separation chamber 10 of FIG. 2B is used.

Figures 4A, 4B, 5A, 5B:
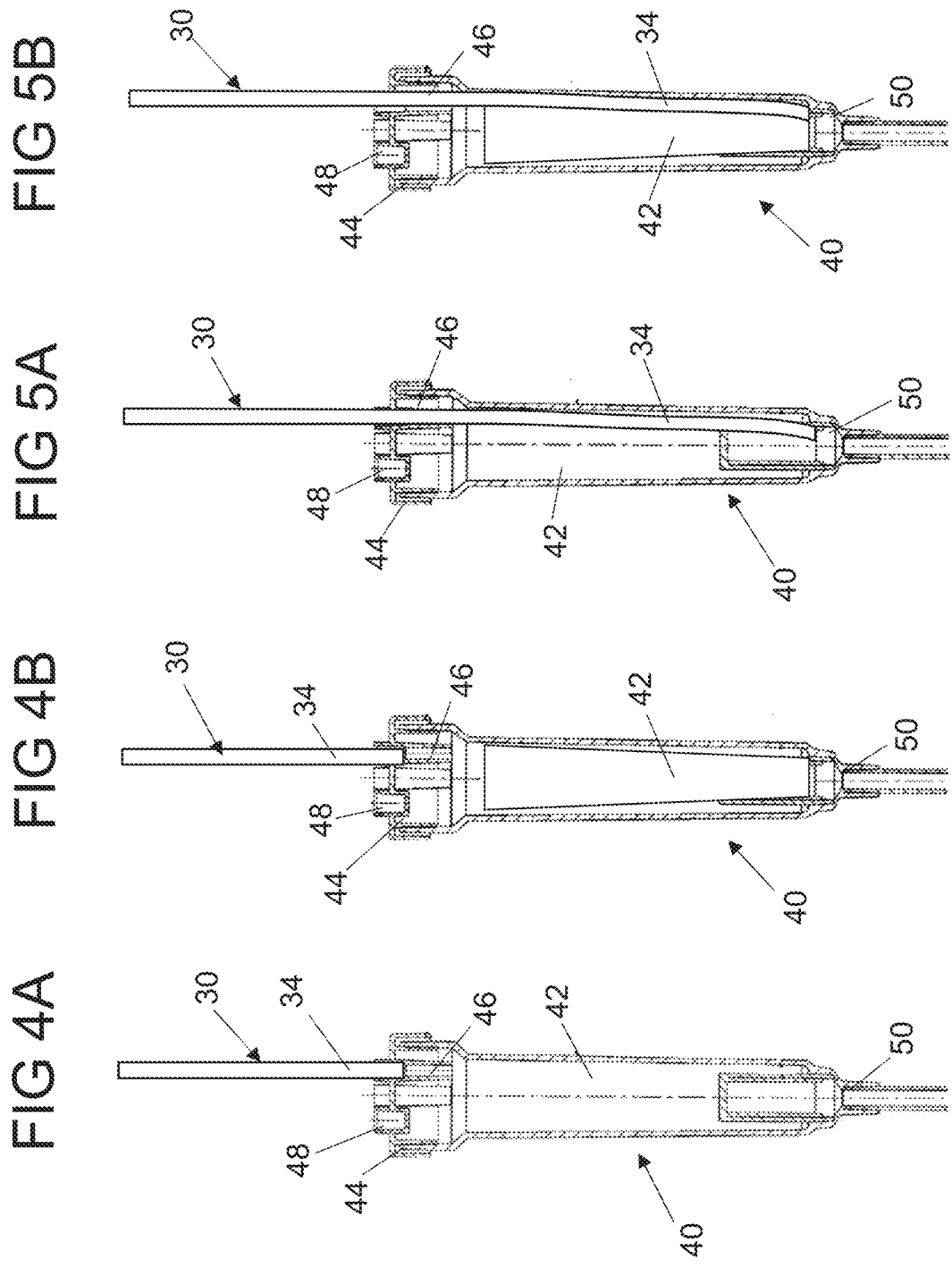
FIGS. 4A, 4B show schematic views of a drip chamber which is commonly used in the prior art.
FIGS. 5A, 5B show schematic views of a drip chamber according to an embodiment of the invention.

FIGS. 4A and 4B show schematic views of a drip chamber 40 which is commonly used in the prior art.

FIG. 4A shows the drip chamber 40 being empty, i.e. there is no fluid in the reservoir 42, while FIG. 4B shows the drip chamber 40 filled with fluid. As it can be seen from FIGS. 4A and 4B, the second end 34 of the red blood cell tube 30 is arranged above the reservoir 42, and thus does not extend into the volume of the reservoir 42 for pressure equalization during pumping from the outlet port for plasma, such as during pumping the MNC layer.

The reservoir 42 is covered by a lid 44 having an inlet 46 to which the second end 34 of the red blood cell tube 30 is attached. The lid 44 comprises a second inlet 48 to accommodate an end of the plasma tube so that also fluid from the plasma tube can be inserted into the reservoir 42. Also, FIGS. 4A and 4B show an outlet opening 50 in a bottom surface of the reservoir 42.

FIGS. 5A and 5B show schematic views of a drip chamber 40 according to an embodiment. Just as already shown before in regard to FIGS. 4A and 4B, the drip chamber 40 shown in FIG. 5A is empty, while FIG. 5B shows the drip chamber 40 filled with fluid.

The drip chamber 40 shown in FIGS. 5A and 5B distinguishes from the drip chamber shown in FIGS. 4A and 4B in that the second end 34 of the red blood cell tube 30 extends into the volume of the reservoir 42 for pressure equalization during pumping. In the shown embodiment, the second end 34 of the red blood cell tube 30 extends approximately into 80% of the volume of the reservoir. In further embodiments, the second end of the red blood cell tube can also extend into the volume of the reservoir 42 to a lesser degree, such as for example only into 20% or 50% of the volume of the reservoir 42. In an alternative embodiment, the second end of the red blood cell tube can also extend to the bottom surface of the reservoir and/or to the outlet opening in the bottom surface of the reservoir.

LIST OF REFERENCE NUMERALS

1 System for Blood Cell Separation
10 Separation Chamber
12 Inlet Port for Blood
14 Outlet Port for Plasma
16 Outlet Port for Cellular Blood Components
18 Further Outlet Port for Cellular Blood Components
20 Blood Pump
22 Plasma Pump
30 Red Blood Cell Tube
32 First End of Red Blood Cell Tube
34 Second End of Red Blood Cell Tube
40 Drip Chamber
42 Reservoir
44 Lid
46 Inlet
48 Second Inlet
20 Outlet Opening
100 Front Panel
102 Centrifuge Compartment

The invention claimed is:
1. System for blood cell separation, comprising:
a separation chamber comprising an inlet port for blood, an outlet port for plasma and at least an outlet port for cellular blood components for the separation of whole blood;
a blood pump for pumping whole blood into the inlet port for blood;
a plasma pump for pumping plasma and/or target cells from the outlet port for plasma out of the separation chamber;
a red blood cell tube comprising a first end and a second end, wherein the first end of the red blood cell tube is connected to the outlet port for cellular blood components for allowing red blood cells to leave the separation chamber; and
a drip chamber comprising a reservoir having a volume and an inlet, wherein the second end of the red blood cell tube is connected to the inlet,
wherein the second end of the red blood cell tube extends into the volume of the reservoir to a bottom surface of the reservoir for pressure equalization during pumping from the outlet port for plasma, wherein the second end extends to an outlet opening in the bottom surface.
2. System according to claim 1 comprising a lid configured to be placed on the reservoir for covering the reservoir, wherein the inlet is arranged in the lid, and wherein the second end of the red blood cell tube extends through the lid.
3. System according to claim 1 wherein the drip chamber comprises a second inlet configured to be connected to a plasma tube which carries fluid from the outlet port for plasma into the reservoir.

4. System according to claim 1 wherein the separation chamber comprises a further outlet port for cellular blood components.

5. Drip chamber for a system for blood cell separation, according to claim 1, comprising:

a reservoir and an inlet, wherein the inlet is connectable to a second end of a red blood cell tube, wherein the second end of the red blood cell tube extends into a volume of the reservoir for pressure equalization during pumping by the system.

* * * * *